(12) United States Patent
Iino et al.

(10) Patent No.: US 7,990,020 B2
(45) Date of Patent: Aug. 2, 2011

(54) ULTRASONIC MOTOR AND ELECTRONIC DEVICE USING THE SAME

(75) Inventors: Akihiro Iino, Chiba (JP); Makoto Suzuki, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 11/999,340

(22) Filed: Dec. 4, 2007

(65) Prior Publication Data

US 2008/0169726 A1 Jul. 17, 2008

(30) Foreign Application Priority Data

Dec. 5, 2006 (JP) .................................. 2006-328362

(51) Int. Cl.
*H02N 2/12* (2006.01)

(52) U.S. Cl. ............ 310/323.04; 310/20; 310/21; 74/20
(58) Field of Classification Search .................... 310/20, 310/21, 323.04; 74/20
See application file for complete search history.

(56) References Cited

U.S. PATENT DOCUMENTS

| 4,623,853 | A | * | 11/1986 | Watanabe et al. ............. 333/151 |
| 5,020,539 | A | * | 6/1991 | Yokoi et al. ................... 600/116 |
| 6,570,296 | B1 | * | 5/2003 | Iino et al. .................. 310/323.03 |
| 2005/0017159 | A1 | * | 1/2005 | Hasegawa et al. ......... 250/231.13 |
| 2008/0001500 | A1 | * | 1/2008 | Moriya et al. ........... 310/323.04 |
| 2008/0024019 | A1 | * | 1/2008 | Sakuma et al. ................. 310/51 |

FOREIGN PATENT DOCUMENTS

| EP | 1768245 | 3/2007 |
| JP | 2006047907 | * 2/2006 |
| WO | 2005114824 | 12/2005 |

* cited by examiner

*Primary Examiner* — Walter Bernson
*Assistant Examiner* — Bryan P Gordon
(74) *Attorney, Agent, or Firm* — Adams & Wilks

(57) ABSTRACT

The present invention provides an ultrasonic motor including a wire having a coiled stator at one end thereof, a vibration generating device disposed at another end of the wire, a moving member that is in contact with the stator, a guide member that guides the rotation of the moving member, and an elastic member that covers the periphery of the wire. Accordingly, the driving efficiency of the ultrasonic motor that has a simple structure and that can be easily downsized can be enhanced and the performance stability thereof can be realized.

20 Claims, 4 Drawing Sheets

ULTRASONIC MOTOR AND ELECTRONIC DEVICE USING THE SAME

BACKGROUND OF THE INVENTION

1. Field of the Invention

The present invention relates to a ultrasonic motor using ultrasonic vibrations of an elastic member as a driving source, and a ultrasonic motor that can be mounted on a small electronic device such as a catheter.

2. Description of the Related Art

The ultrasonic motor using ultrasonic vibrations of an elastic member as a driving source, with various features which an electromagnetic motor does not have, has been increasingly applied to diverse fields such as electronic devices including a driving source of an autofocus mechanism of a camera, and a medical device that is exposed to an electromagnetic environment. Also, since the ultrasonic motor is easily downsized and has a high degree of freedom in shape, new type ultrasonic motors have been actively researched and developed.

Among the new type ultrasonic motors, it is expected that an ultrasonic motor of a type that transmits ultrasonic vibrations through an acoustic waveguide to a coiled stator and drives a moving member that is disposed in the vicinity of the stator (WO 2005/114824) is applied to, for example, a catheter that can be inserted into an extremely thin portion such as a blood vessel within a human body since the ultrasonic motor can be downsized, and an energy can be supplied from a remote location.

However, the ultrasonic motor of the type which transmits the ultrasonic vibrations to the coiled stator through the acoustic waveguide and drives the moving member that is disposed in the vicinity of the stator cannot efficiently drive the moving member because the ultrasonic vibrations that have been transmitted from the acoustic waveguide are attenuated or affected by reflected waves for the following reasons.

1) A wire that is an acoustic waveguide comes in contact with another member to attenuate the vibrations.

2) The vibrations that have been transmitted through the acoustic waveguide are reflected on a boundary between the stator (coiled) and the acoustic waveguide.

3) The vibration that has been transmitted to the stator is reflected by an end portion of the stator, and is mixed with the vibrations that are transmitted to the stator.

Also, the shape of a coil that constitutes the stator is changed during driving, and the output of the ultrasonic motor is not stabilized.

An object of the present invention is to provide an ultrasonic motor that is simple in structure and high in output and reliability.

SUMMARY OF THE INVENTION

To solve the above-mentioned problems, according to the present invention, there is provided an ultrasonic motor, including: a wire having a coiled stator at one end thereof; a vibration generating device disposed at another end of the wire; a moving member that is in contact with the stator; a guide member that guides the rotation of the moving member; and an elastic member that covers the periphery of the wire.

With the above structure, the output of the ultrasonic motor is stabilized irrespective of the use state because the attenuation of the vibrations which are transmitted to the stator can be suppressed even if the wire comes in contact with another member.

Further, according to the present invention, there is provided an ultrasonic motor including: a wire having a coiled stator at one end thereof; a vibration generating device disposed at another end of the wire; a moving member that is in contact with the stator; a guide member that guides the rotation of the moving member; and a fixing portion that is disposed in the guide member and fixes a part of the wire.

With the above structure, the output of the ultrasonic motor is stabilized because the shape of the coil that constitutes the stator during driving remains stable.

Still further, according to the present invention, there is provided an ultrasonic motor which may include: a wire having a coiled stator at one end thereof; a vibration generating device disposed at another end of the wire; a moving member that is in contact with the stator; a guide member that guides the rotation of the moving member; and a vibration absorbing member that is disposed on an end of the stator.

With the above structure, since the vibrations that have been transmitted to the stator are prevented from being reflected by the end of the stator, the efficiency of the ultrasonic motor may be improved.

In the ultrasonic motor of the present invention, the vibration absorbing member may be a movement regulation member. According to the ultrasonic motor of the present invention, the number of parts can be reduced, and a smaller ultrasonic motor can be realized.

Yet further, according to the present invention, there is provided an ultrasonic motor, which may include: a wire having a coiled stator at one end thereof; a vibration generating device disposed at another end of the wire; a moving member that is in contact with the stator; a guide member that guides the rotation of the moving member; and a second coil portion that is different in shape from a coil that constitutes the coiled stator, and continuous to the coiled stator.

In the ultrasonic motor of the present invention, an outer diameter of the second coil portion may be smaller than an outer diameter of the coiled stator. Also, an outer diameter of the second coil portion may become larger toward the coiled stator.

In addition, in the ultrasonic motor of the present invention, a coil pitch the second coil portion may be larger than a coil pitch of the coiled stator. Also, a coil pitch of the second coil portion may become smaller toward the coiled stator.

In the ultrasonic motor of the present invention, when the second coil portion is disposed between the stator and the vibration generating device, the vibrations that are transmitted from the vibration generating device can be smoothly transmitted to the stator without being attenuated at the end of the stator. Also, when the second coil portion is disposed at the other end of the stator (opposite to the vibration generating device), it is possible to prevent the reflection at the end of the stator because the vibrations that have been transmitted to the stator from the vibration generating device can be attenuated at the second coil portion.

According to the present invention, the ultrasonic motor that is extremely small in size and high in output can be obtained with a simple structure, and the performance stability of the ultrasonic motor can be improved. As a result, the present invention can be applied to electronic devices that are extremely small in the size and require the high reliability.

DETAILED DESCRIPTION OF THE PREFERRED EMBODIMENTS

Hereinafter, a description will be given of embodiments of the present invention with reference to the accompanying drawings.

First Embodiment

Figure 1A:
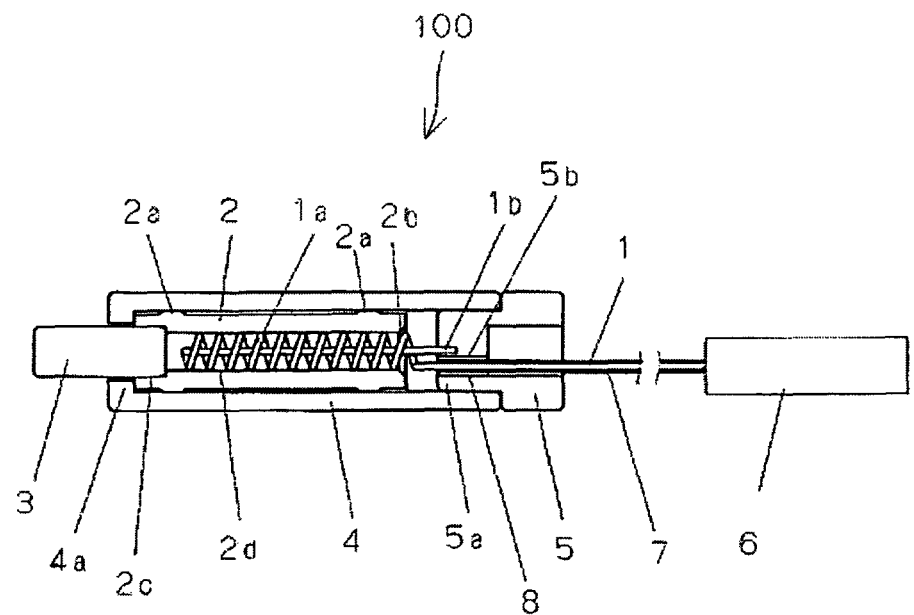
FIGS. 1A and 1B are diagrams showing the structure of an ultrasonic motor according to a first embodiment of the present invention.

The structure and driving principle of an ultrasonic motor 100 according to a first embodiment of the present invention will be described with reference to FIGS. 1A and 1B. The ultrasonic motor 100 of the present invention includes a wire 1 having a coiled stator 1a at one end, a vibration generating device 6 that is disposed at the other end of the wire 1 and functions as a vibration source, a moving or movable member 2 of substantially cylindrical shape which is disposed around the outer periphery of the stator 1a, a guide member 4 that guides the rotation of the moving member 2, a movement regulation member S that is disposed at the end of the guide member 4, and an output member 3 that extracts the rotation output of the moving member 2.

When the vibration wave is input to the wire 1 from the vibration generating device 6, the vibration wave is transmitted to the coiled stator 1a. The surface of the stator 1a is elliptically moved by the transmission of the vibration wave. Because the direction of the elliptic motion is opposite to the advancing direction of the vibration waves, the moving member 2 rotates in that direction. Projections 2a are disposed on the entire outer circumference of the moving member 2 in the circumferential direction, and rotatably guided in the inner circumference of the guide member 4. The leading end of the moving member 2 is fixed with the output member 3 and rotated together with the moving member 2. The movement of the moving member 2 in the rotation center axial direction is conducted by a regulation portion 4a that is disposed at one end of the guide member 4 and a convex portion 5a of the movement regulation member 5 which is fixed to the other end of the guide member 4.

As long as the elliptic motion can occur on the surface of the stator 1a, the structure of the vibration generating device 6 is not limited. However, it is preferable to use vertical vibrations that are excited by a Langevin vibrator that can output a large output.

Figure 1B:
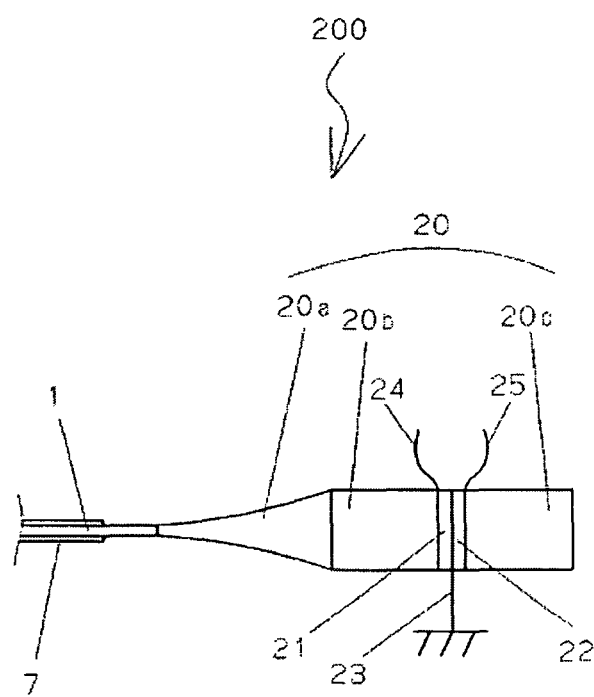

FIG. 1B is a diagram showing an arranging method when a Langevin vibrator 200 is used as the vibration generating device 6. A wire 1 is fixed to the leading end of the Langevin vibrator 200 (horn 20a) by welding, and the vertical vibrations are transmitted to the longitudinal direction of the wire 1, that is, the direction of the stator 1a. The Langevin vibrator 200 includes cylindrical blocks 20b and 20c that are so arranged as to sandwich two disk piezoelectric elements 21 and 22 and constitute a vibration body 20 made of metal such as duralumin, and a horn 20a that is fixed to the cylindrical block 20b by means of a bolt not shown, welding, or the like. The horn 20a is thinned toward the leading end (joint portion with the wire 1), and enlarges the vibrations. The piezoelectric elements 21 and 22 are disposed between the cylindrical blocks 20b and 20c, and the cylindrical blocks 20b and 20c are fastened to each other by a bolt not shown, and fixed in a state where the compression force is applied. Electrodes not shown are disposed on the overall front and rear surfaces of the piezoelectric elements 21 and 22, and the electrodes are rendered conductive to the external by means of the lead wires 23, 24, and 25. The polarization of the piezoelectric elements 21 and 22 are made in the thickness direction, and the polarization directions are opposite to each other. The lead wire 23 is grounded, and an AC signal of the resonance frequency of the Langevin vibrator 200 is applied to the lead wires 24 and 25, to thereby excite the vertical vibrations in the vibration body 20. When the vertical vibrations that are propagated on the wire 1 are input to the stator 1a, the curved vibration wave is induced due to the presence of the curve of the wire that constitutes the stator 1a (coil), which generates the elliptic motion. In this way, because the vertical vibrations are transmitted to the wire 1, it is difficult to attenuate the vibrations when the wire 1 comes in contact with another member, and even if the wire is made longer, the vibration waves can be efficiently transmitted from the vibration generating device 6 to the stator 1a.

In the ultrasonic motor 100 according to the present invention, the surface of the wire 1 is covered with an elastic member 7 such as silicon rubber or urethane resin, which has extremely smaller elasticity than the wire 1. According to this configuration, even if the wire 1 comes in contact with another member while the ultrasonic motor 100 is being driven, the attenuation of the vibrations that are transmitted to the stator 1a can be suppressed. As a result, the output of the ultrasonic motor 100 is stabilized not depending on the use state.

Also, a part of the wire 1 (close to the boundary with the stator 1a) is fixed to a fixing portion 5b that disposed in the guide member 4. The fixing portion 5b includes a hole through which the wire 1 is inserted. The hole is filled with an adhesive 8 such as silicon rubber or urethane resin, or an elastic member such as silicon rubber to fix the wire 1. With the above configuration, the wire 1 can be fixed without attenuating the vibrations. With this structure, because the leading end of the stator 1a does not come in contact with the output member 3, and the shape of the coil that constitutes the stator 1a during driving is stabilized, the output of the ultrasonic motor is stabilized. Incidentally, this structure is required when the movement regulation member 5 is made of plastic or metal. However, when the movement regulation member 5 per se is formed of an elastic member such as silicon rubber or urethane resin, the adhesive 8 is not required, and the wire 1 is fixed by pressure by the movement regulation member 5 per se.

Also, the wire 1b that extends from the end of the stator 1a is bent toward the vibration generating device 6 side, and fixedly inserted into the movement regulation member 5. The movement regulation member 5 is formed of the elastic member such as silicon rubber or urethane resin. However, when the movement regulation member 5 is made of a hard plastic or metal, an adhesive that is low in the hardness such as silicon rubber is filled between the wire 1b and the movement regulation member 5. With this structure, since the vibrations that are transmitted to the stator 2 can be prevented from being reflected by the end of the stator 1, the efficiency of the ultrasonic motor is improved. Also, when the movement regulation member 5 per se is formed of a vibration absorbing member, it is possible to reduce the number of parts, and the smaller ultrasonic motor can be realized.

Second Embodiment

A second embodiment of the present invention will be described with reference to FIGS. 2A and 2B. In this embodiment, because the basic structure of the ultrasonic motor is identical with that shown in the first embodiment, its description will be omitted, and the only configurations of the wire 1 and the moving member 2 will be described.

The coiled stator 1a is placed in the inner diameter portion of the moving member 2. The stator 1a and the inner diameter portion of the moving member 2 come in pressure contact with each other, and the moving member 2 is frictionally driven by the vibration waves that are generated by the stator 1a.

Figure 2A:
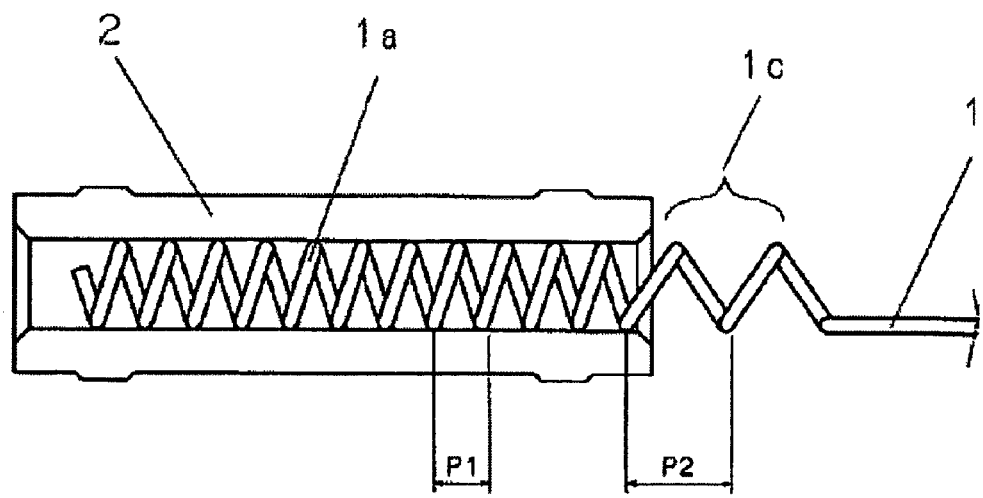
FIGS. 2A and 2B are diagrams showing a relationship between a moving member and a stator in an ultrasonic motor according to a second embodiment of the present invention.
Figure 2B:
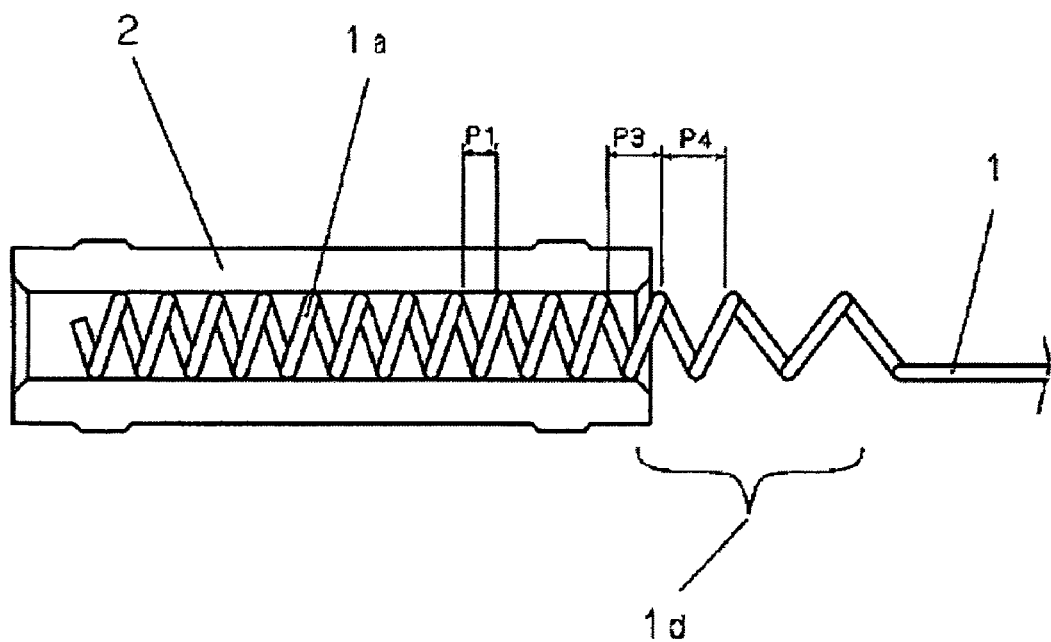

Referring to FIG. 2A, a second coil portion 1c that is continuous to the stator 1a and different in the pitch of the coil from the stator 1a is disposed at a side of the vibration generating device 6 not shown rather than the stator 1a.

The pitch P2 of the second coil portion 1c is larger than the pitch P1 of the coil of the stator 1a. With the above configuration, it is possible to smoothly transmit the vibration waves that are transmitted from the vibration generating device 6 to the stator 1a without attenuation at the end of the stator 1a. Also, the above effect is larger in the case where the second coil portion 1c is replaced with a second coil portion 1d in which pitches are gradually increased to P3 and P4 (both pitches are larger than the pitch P1), as shown in FIG. 2B.

Note that, the description has been made of the structure in which the stator 1a is placed in the inner diameter portion of the moving member 2. Similarly, this embodiment can be applied to an ultrasonic motor having a structure in which the moving member 2 is placed in the inner diameter portion of the stator 1a.

Third Embodiment

A description will be given of a third embodiment of the present invention with reference to FIGS. 3A and 3B. In this embodiment, because the basic structure of the ultrasonic motor is identical with that in the first and second embodiments, its description will be omitted, and only the configurations of the wire 1 and the moving member 2 will be described.

Figure 3A:
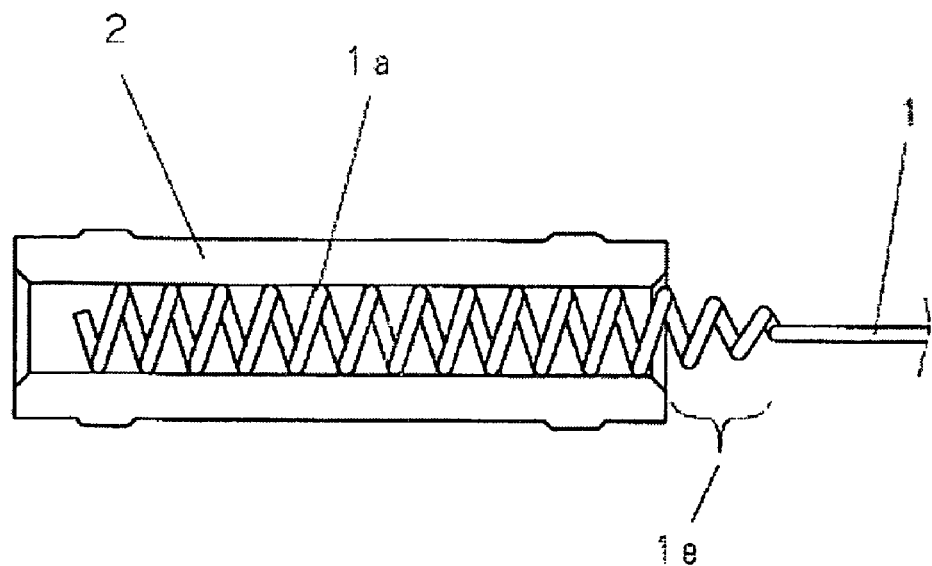
FIGS. 3A and 3B are diagrams showing a relationship between a moving member and a stator in an ultrasonic motor according to a third embodiment of the present invention.
Figure 3B:
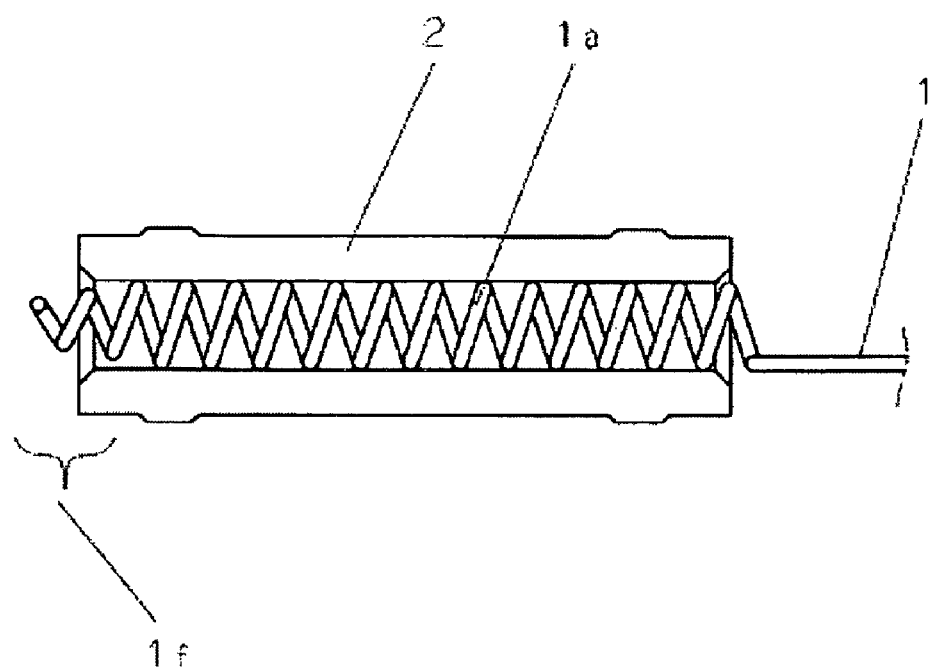

Referring to FIG. 3A, a second coil portion 1e that is continuous to the stator 1a and gradually increases the outer diameter as compared with the stator 1a is disposed at a side of the vibration generating device 6 not shown rather than the stator 1a.

With the above structure, it is possible to smoothly transmit the vibration waves that are transmitted from the vibration generating device 6 to the stator 1a without attenuation at the end of the stator 1a. Also, the second coil portion 1e can be replaced with a second coil portion that is smaller in outer diameter than the stator 1a and constant in outer diameter.

Also, when the second coil portion 1f is disposed at the end surface opposite to the vibration generating device 6 of the stator, the vibration waves that are transmitted from the vibration generating device 6 to the stator 1a can be attenuated at the second coil portion 1f. As a result, it is possible to prevent the reflection of the vibration waves at the end of the stator. The second coil portion 1f has the outer diameter gradually reduced as shown in FIG. 3B. However, the second coil portion 1f can be formed of a second coil portion entirely having an outer diameter smaller than the outer diameter of the stator 1a, or can be formed of a second coil portion having a larger pitch than the pitch of the stator 1a (the coil portion may entirely have the same pitches or gradually increase the pitches).

Fourth Embodiment

Figure 4:
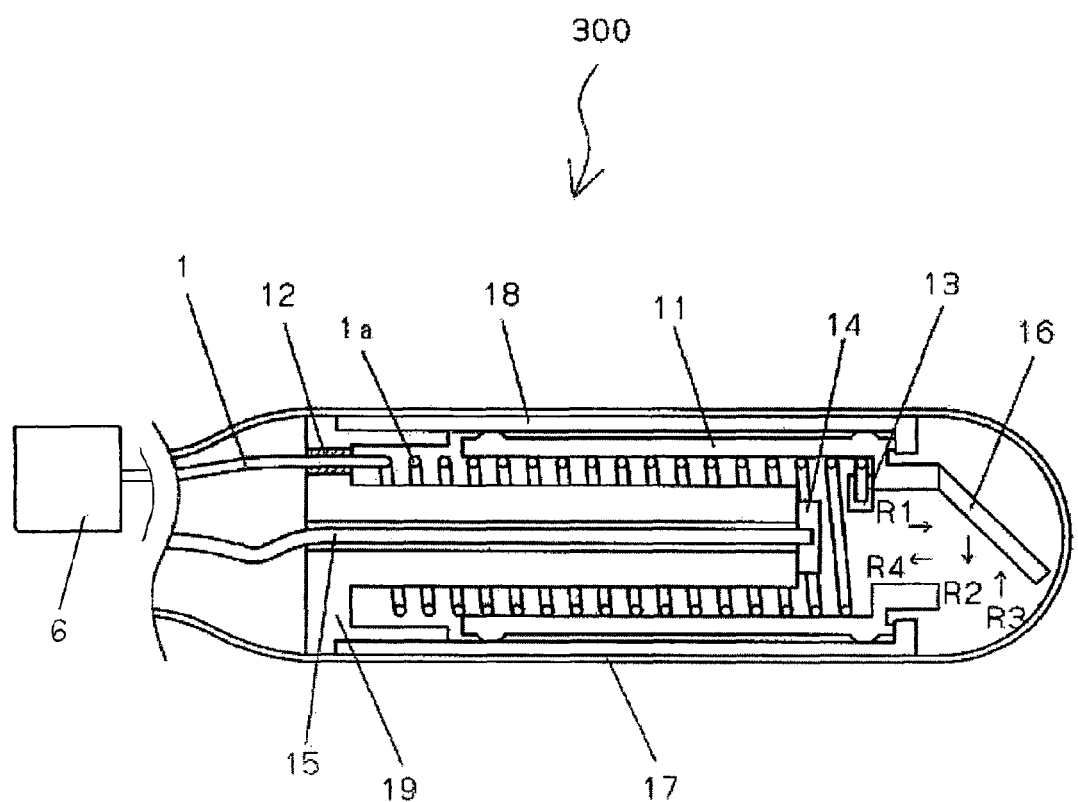
FIG. 4 is a diagram showing the structure of a catheter using an ultrasonic motor according to a fourth embodiment of the present invention.

Subsequently, a description will be given of an ultrasonic endoscope 300 as a representative of the catheter which is the electronic device using the ultrasonic motor of the present invention. FIG. 4 is a diagram showing a section of the catheter. The catheter 300 includes a coiled stator 1a, a moving or movable member 11 that is disposed around the outer periphery of the stator 1a, a guide member 18 that guides the rotation of the moving member 11, a movement regulation member 19 that fixes the guide member 18 as well as a vibrator that is disposed inside of the stator 1a, and regulates the movement of the moving member 11 in the rotational axial direction. As illustrated in FIG. 4, the movable or moving member 11 has a hollow cylindrical shape having inner and outer surfaces and encircles the coiled stator 1a with the inner surface in contact with the surface of the coiled stator. The catheter 300 also includes a lead wire 15 for inputting an electric signal to the vibrator 14 from the outside and obtaining the electric signal that is output from the vibrator 14, a reflector 16 that is fixed to the leading end of the moving member 11, an adhesive 12 that is filled in the hole of the movement regulation member 19 and fixes the wire 1, a vibration absorbing member in the form of an acoustic absorbent 13 that is fixed to the end of the stator 1a and made of silicon rubber, and a cover 17 that entirely covers the above parts.

When the ultrasonic waves are radiated from the vibrator 14 that is formed of piezoelectric elements (arrow R1), the ultrasonic waves are reflected by the reflector 16, changed in a direction indicated by an arrow R2, radiated, and impinge on the inner wall of the blood vessel. Further, after the ultrasonic waves (R3) that have been reflected by the inner wall are again input to the mirror and reflected, the ultrasonic waves are input to the vibrator 14 (R4). The operation is conducted while the reflector 16 that is fixed to the moving member 11 is rotated, and the output signal of the vibrator 14 is analyzed, thereby making it possible to obtain the information on the entire periphery of the blood vessel inner wall. The interior of the case 17 is filled with a solution close to the acoustic impedance within the blood vessel, and even under the environments, the ultrasonic motor of the present invention is stably operated.

Also, the ultrasonic motor of the present invention does not supply an energy to the stator by the supply of an electric power by a lead wire, but conducts the ultrasonic vibrations through a wire. Accordingly, when the vibration source 6 is disposed outside the body, there is no influence of temperature rising due to the electric power on the body interior, and there is no fear that a current flows into the body interior. Accordingly, the vibration source can be used within the body at ease.

In this embodiment, the description has been made of the example in which the acoustic absorbent 13 is disposed at the end of the stator 1a among the ultrasonic motor shown in the above embodiment. Alternatively, the structure of the ultrasonic motor according to another embodiment may be applied.

The ultrasonic motor according to the present invention supplies the energy to the stator by inputting not the electric power but the ultrasonic vibration per se, and can supply the energy from a remote location. Therefore, it is possible to apply the ultrasonic motor to, for example, a catheter that is inserted into the blood vessel of the human body. Also, because the structure is simple and the size is small, the present invention is applicable to the driving source of another small electronic device.

What is claimed is:

1. An ultrasonic motor, comprising:
   a coiled stator having one end thereof connected to a wire;
   a vibration generating device that generates vibration waves and propagates them along the wire and the coiled stator;
   a moving member that is in contact with the coiled stator;
   a guide member that guides the rotation of the moving member; and
   a vibration absorbing member disposed on the other end of the coiled stator.

2. An ultrasonic motor according to claim 1; including an elastic member that covers the periphery of the wire.

3. An ultrasonic motor according to claim 1; including a fixing portion that is disposed in the guide member and fixes a part of the wire.

4. An ultrasonic motor according to claim 1; wherein the vibration absorbing member comprises the guide member.

5. An ultrasonic motor according to claim 1; wherein the coiled stator terminates at one end in a second coil portion that is different in shape from a first coil portion that constitutes the coiled stator.

6. An ultrasonic motor according to claim 5; wherein an outer diameter of the second coil portion is smaller than an outer diameter of the coiled stator.

7. An ultrasonic motor according to claim 5; wherein a coil pitch of the second coil portion is larger than a coil pitch of the coiled stator.

8. An ultrasonic motor according to claim 5; wherein an outer diameter of the second coil portion becomes progressively larger in a direction toward the coiled stator.

9. An ultrasonic motor according to claim 5; wherein a coil pitch of the second coil portion becomes progressively smaller in a direction toward the coiled stator.

10. An ultrasonic motor according to claim 5; wherein the second coil portion is disposed between the stator and the vibration generating device.

11. An electronic device comprising an ultrasonic motor according to claim 5.

12. An electronic device that includes an ultrasonic motor according to claim 1.

13. An ultrasonic motor, comprising: a coiled stator having two ends; a wire connected to one end of the coiled stator; a vibration generating device that generates vibration waves and propagates them along the wire and the coiled stator to cause the surface of the coiled stator to undergo elliptic motion; a movable member in contact with the coiled stator and rotationally driven by the elliptic motion of the surface of the coiled stator; and a vibration absorbing member disposed on the other end of the coiled stator and that absorbs vibration waves propagated along the wire to the other end of the coiled stator to prevent the vibration waves from being reflected by the other end of the coiled stator.

14. An ultrasonic motor according to claim 13; wherein the vibration absorbing member is an acoustic absorbent.

15. An ultrasonic motor according to claim 13; wherein the vibration absorbing member is made of rubber.

16. An ultrasonic motor according to claim 13; wherein the movable member has a hollow cylindrical shape having inner and outer surfaces and encircles the coiled stator with the inner surface in contact with the surface of the coiled stator.

17. An ultrasonic motor according to claim 16; further including a guide member that guides the rotation of the movable member.

18. An ultrasonic motor according to claim 13; further including a guide member that guides the rotation of the movable member.

19. An electronic device having an ultrasonic motor according to claim 13.

20. An electronic device according to claim 19; wherein the electronic device is an endoscope having a catheter, the catheter having at its distal end a cover that covers the ultrasonic motor, the ultrasonic motor having a reflector connected to rotate with the movable member and a vibrator that produces ultrasonic waves which are directed onto the reflector and reflected by the reflector to a region outside the cover.

* * * * *